United States Patent
Weiler et al.

(10) Patent No.: US 10,987,157 B2
(45) Date of Patent: Apr. 27, 2021

(54) COAGULATION AND DISSECTING INSTRUMENT WITH IMPROVED CONTROL

(71) Applicant: Erbe Elektromedizin GmbH, Tübingen (DE)

(72) Inventors: Rolf Weiler, Kusterdingen (DE); Martin Fritz, Tübingen (DE); Heiko Schall, Nürtingen (DE)

(73) Assignee: Erbe Elektromedizin GmbH, Tübingen (DE)

(*) Notice: Subject to any disclaimer, the term of this patent is extended or adjusted under 35 U.S.C. 154(b) by 265 days.

(21) Appl. No.: 15/241,892

(22) Filed: Aug. 19, 2016

(65) Prior Publication Data
US 2017/0049505 A1    Feb. 23, 2017

(30) Foreign Application Priority Data
Aug. 21, 2015 (EP) .................................. 15182008

(51) Int. Cl.
*A61B 18/00* (2006.01)
*A61B 18/14* (2006.01)
*A61B 18/12* (2006.01)

(52) U.S. Cl.
CPC ............... *A61B 18/1445* (2013.01); *A61B 2018/00607* (2013.01); *A61B 2018/00708* (2013.01);
(Continued)

(58) Field of Classification Search
CPC ........... A61B 2018/00696; A61B 2018/00607; A61B 2018/00916; A61B 18/085;
(Continued)

(56) References Cited

U.S. PATENT DOCUMENTS

| | | | |
|---|---|---|---|
| 4,244,371 A | 1/1981 | Farin | |
| 6,174,309 B1* | 1/2001 | Wrublewski | ....... A61B 18/1442 606/45 |

(Continued)

FOREIGN PATENT DOCUMENTS

| | | |
|---|---|---|
| CN | 1913840 A | 2/2007 |
| CN | 101180003 A | 5/2008 |

(Continued)

OTHER PUBLICATIONS

European Office Action in corresponding European Application No. 15 18 2008, dated Jul. 6, 2018, with English Transtation, 13 pages.
(Continued)

*Primary Examiner* — Jaymi E Della
*Assistant Examiner* — Rachel A. Vierra
(74) *Attorney, Agent, or Firm* — Fitch, Even, Tabin & Flannery LLP (57) ABSTRACT

The coagulation arrangement (10) according to the invention comprises an instrument (11) having a tool (17) comprising coagulating electrodes (22, 23, 27, 28), as well as a dissecting electrode (36). The electrodes are powered by a circuit (44) that comprises a coagulating voltage source (54) and a dissecting voltage source (55), or that can be connected to such sources. The device comprises a dissection actuating switch (60) and a coagulation actuating switch (59). The former is connected to a power switch (58) that—in dissecting mode—connects the current path from the dissecting voltage source (55) to the dissecting electrode (36), before the dissecting voltage source (55) or the HF output voltage source (47) and the coagulating voltage source (54) are actuated. Thus, the user is presented with a reliable means in a simple manner in order to be able to more flexibly perform more complex operations.

12 Claims, 9 Drawing Sheets

(52) U.S. Cl.
CPC .......... *A61B 2018/00922* (2013.01); *A61B 2018/00928* (2013.01); *A61B 2018/00952* (2013.01); *A61B 2018/00958* (2013.01); *A61B 2018/1286* (2013.01); *A61B 2018/1457* (2013.01); *A61B 2018/1467* (2013.01)

(58) Field of Classification Search
CPC .......... A61B 18/14; A61B 2018/00708; A61B 2018/00922; A61B 2018/00928; A61B 2018/00952; A61B 2018/00958; A61B 2018/1286; A61B 2018/1457; A61B 2018/1467; A61B 18/1445
See application file for complete search history.

(56) References Cited

U.S. PATENT DOCUMENTS

| | | | | |
|---|---|---|---|---|
| 7,204,835 | B2* | 4/2007 | Latterell | A61B 18/1445 606/45 |
| 7,214,224 | B2* | 5/2007 | Goble | A61B 18/1206 606/34 |
| 8,002,769 | B2* | 8/2011 | Goble | A61B 18/1206 606/37 |
| 8,361,065 | B2 | 1/2013 | West, Jr. | |
| 8,394,094 | B2 | 3/2013 | Edwards et al. | |
| 2005/0171533 | A1 | 8/2005 | Latterell et al. | |
| 2008/0195093 | A1 | 8/2008 | Couture et al. | |
| 2009/0076504 | A1* | 3/2009 | Schnitzler | A61B 18/1402 606/45 |
| 2013/0274729 | A1* | 10/2013 | Orszulak | A61B 18/1445 606/33 |
| 2014/0018795 | A1* | 1/2014 | Shilev | A61B 18/1402 606/41 |
| 2014/0214019 | A1 | 7/2014 | Baxter, III et al. | |
| 2016/0249975 | A1 | 9/2016 | Konishi et al. | |

FOREIGN PATENT DOCUMENTS

| | | |
|---|---|---|
| CN | 102164556 A | 8/2011 |
| EP | 1958583 A2 | 8/2008 |
| EP | 2792326 A1 | 10/2014 |
| JP | S50-074195 U | 6/1975 |
| JP | S57-185852 A | 11/1982 |
| JP | H08-317935 A | 12/1996 |
| JP | 2008-212663 A | 9/2008 |
| JP | 2014-241187 A | 12/2014 |
| WO | 0047124 A1 | 8/2000 |
| WO | 2015093409 A1 | 6/2015 |

OTHER PUBLICATIONS

European search report in corresponding European Application No. 15 18 2008, dated Feb. 4, 2016, 14 pages.
Chinese Office Action dated Dec. 18, 2019, in corresponding Chinese Application No. 201610697052.8, with English translation (15 pages).
Japanese Notice of Reasons for Refusal dated Jan. 14, 2020, in corresponding Japanese Application No. 2016-159715, with English translation (15 pages).
Chinese Office Action dated Jul. 24, 2020, in corresponding Chinese Application No. 201610697052.8, with English translation (25 pages).
Japanese Search Report dated Dec. 12, 2019, in corresponding Japanese Application No. 2016-159715 (18 pages).

* cited by examiner

COAGULATION AND DISSECTING INSTRUMENT WITH IMPROVED CONTROL

RELATED APPLICATION(S)

This application claims the benefit of European Patent Application No. 15182008.1 filed Aug. 21, 2015, the contents of which are incorporated herein by reference as if fully rewritten here.

TECHNICAL FIELD

The invention relates to an instrument for dissecting and coagulating or, if needed, only for coagulating biological tissue.

BACKGROUND

Instruments for coagulating and dissecting biological tissue have been known, for example, for document U.S. Pat. No. 8,394,094 B2. The instrument is configured so as to represent a type of forceps, wherein tissue grasped with the branches of said forceps is coagulated by means of electrical current. To do so, coagulating electrodes, as well as a dissecting electrode, are provided on one of the branches. The other branch acts as a counterelectrode.

A similar instrument has been known from document WO 00/47124. The instrument comprises a transformer arrangement that is fed by an electrical generator. The transformer arrangement generates both the coagulating voltage and the dissecting voltage. In doing so, coagulation and dissection can be performed simultaneously.

Another instrument belonging to the same genus has been known from document EP 1 958 583 A2, the tool of said instrument again comprising coagulating electrodes and at least one dissecting electrode. A switch array is used for actuation, said switch array being provided on the handle of the instrument and allowing the actuation of the electrodes.

Regarding the electronic control of the coagulating and dissecting process, publication US 2005/0171533 A1 discloses an instrument with a coagulating and dissecting electrode that are powered by an HF generator. The instrument comprises a control arrangement actuating two switches in sequence in order to initially actuate the coagulating electrodes and then the dissecting electrode. Control of the actuation is effected by tapping transformer windings.

In practical applications it may be desirable to manually control the processes of coagulation and dissection. In doing so, it may happen that the user, for example, wishes to perform only a coagulation or only a dissection or that he wishes to perform another coagulation and dissection thereafter.

SUMMARY

The object of the invention is to name an instrument that allows a reliable manual control of the coagulating and dissecting processes, wherein the aim is a technically most simple solution.

The instrument according to the invention can be used, as needed, for coagulating and dissecting biological tissue. Said instrument comprises a tool with at least two coagulating electrodes, one of which being movable relative the other, so that—viewed overall—they can be moved relative to each other. They are disposed to grasp tissue between them and, if desired, mechanically compress said tissue. Furthermore, at least one dissecting electrode is provided for dissecting the tissue grasped between the coagulating electrodes as needed.

Provided in the instrument is an electrical circuit that is connected, on the output side, to the coagulating electrodes and to the dissecting electrode. On the input side, a power supply source can be connected to the electrical circuit. Preferably, the supply voltage source is an HF output voltage source. The HF output voltage source supplies a dissecting voltage source, as well as a coagulating voltage source that may be a component of the electrical circuit. However, it is also possible to provide the dissecting voltage source and the coagulating voltage source externally, in which case the instrument can be connected to these sources by means of its electrical circuit. The dissecting voltage source and the coagulating voltage source may be the outputs of a transformer that is connected, on its input side, to the HF output voltage source. The transformer may be arranged in the instrument. Alternatively, it may also be accommodated outside the instrument, for example, in a plug adapter or in a supply device.

The electrical circuit comprises a power switch for the selective disconnection or connection of the cutting electrode or of the dissecting voltage source, as well as a switch for the selective actuation of the coagulating voltage source or the HF output voltage source. A transformer provided in the instrument may act as the coagulating voltage source and, at the same time, be powered by the coagulating voltage that can be delivered by the HF output voltage source. The actuation of the coagulating voltage source may be direct in that the coagulating voltage source (e.g., the transformer) may be actuated as such (switched on and off). Preferably, the actuation is indirect in that the coagulation actuating switch is disposed for the actuation (and deactuation) of the HF output voltage source that is, for example, an HF generator of a medical supply device that is connected to the instrument. When the instrument receives supply voltage from the HF output voltage source, the coagulating voltage source is active.

In the instrument according to the invention the power switch and the control switch are serially controlled by a common actuating element for the actuation of the coagulating voltage source. The control switch may be a coagulation actuating switch or a dissection actuating switch. The serial control of the control switch and the power switch is understood to mean that a manual actuation of the actuating element initially has the result that one of the switches, preferably the power switch, is actuated, i.e., opened or closed, and that the switch for actuating the coagulating voltage source is closed only thereafter, i.e., when the power switch has already interrupted or has already closed the electrical current path leading to the dissecting electrode. In this manner, the dissecting electrode is disconnected from the dissecting voltage source during coagulation, i.e., before an actuation of the HF output voltage source takes place, for example. In the alternative embodiment comprising a power switch acting as the closer, the dissecting electrode is connected to the dissecting voltage source, before an actuation occurs. Consequently, the coagulating voltage source and the dissecting voltage source can be actuated simultaneously—without the dissecting electrode receiving dissecting voltage while in coagulating mode.

Based on this concept, it is possible to produce a highly reliably working and sensitively controlled instrument with a particularly simple circuit, wherein said instrument can be connected to an HF generator two-pole output and can be selectively used for coagulation as well as for dissection, in which case the mode reversal can be accomplished directly on the instrument with the simplest means.

In the instrument according to the invention the power switch and the coagulation actuating switch are connected to the actuating element in such a manner that—when the actuating element is actuated—the power switch will open first, before the coagulation actuating switch closes, and that, when the actuating element is cleared the coagulation actuating switch will open, before the power switch closes. This ensures that—in a strict coagulating mode—the dissecting electrode is always disconnected from the dissecting voltage source, i.e., irrespective of whether it is in fact active or not. Considering the mentioned concept, the possibility of configuring and providing the dissecting voltage source at a circuit location that is coupled in a fixed manner with the coagulating voltage opens up—i.e., viewed from the transformatory perspective, in which case the coagulating voltage is delivered by the HF output voltage source. This results in a simple design of the instrument.

The power switch that conducts the dissecting current, i.e., connects the dissecting voltage source to the dissecting electrode is preferably a normally closed contact. This means that—in not actuated state (resting state) it establishes an electrical connection between the dissecting voltage source and the dissecting electrode. In contrast, in actuated state, it disconnects the dissecting electrode from the dissecting voltage source. In actuated state it assumes the coagulating mode. In this mode, it can connect the dissecting electrode with the coagulating voltage source. In this case, the dissecting electrode may contribute to the coagulating effect. However, it may also be desirable to apply a voltage to the dissecting electrode in coagulating mode, said voltage being lower than the coagulating voltage, in order to thus preclude any dissecting effect. In doing so, the power switch—in actuated state—can connect the dissecting electrode to a low-voltage source that makes available a reduced voltage. This reduced voltage, for example, may be a fraction of the coagulating voltage, e.g., 75% or 50% thereof. The low-voltage source may be a transformer that is supplied by the coagulating voltage on the primary side. The transformer may be configured as an autotransformer, so that the low-voltage source is a tapping of a winding to which the coagulating voltage is applied.

It is also possible that the power switch connects the dissecting electrode, in actuated state of the coagulation actuating switch via a power limiting means, to the dissecting voltage source or to the coagulating voltage source. The power limiting means may be a capacitor, an ohmic resistor, a non-linear resistor, an inductive component or a combination of two or more of the mentioned components. In any event, it is dimensioned such that it limits the current conducted to the dissecting electrode in the coagulating mode to a value that does not result in the dissection of tissue.

Alternatively, it is also possible to switch the dissecting electrode in the coagulating mode potential-free, i.e., not connected to any source of electricity. In this case, the dissecting electrode does not share in the coagulating process so that a lower or no tissue shrinkage occurs in the region of the dissecting electrode.

In general, it is advantageous if the dissecting electrode and a potentially existing counterbearing are configured so as to be resilient relative on each other. For example, the dissecting electrode may be resiliently supported in order to be movable in closing direction of the branch, Additionally or alternatively, the counterbearing may also be arranged so as to be movable or be elastically configured in order to be able to also yield to the dissecting electrode into the direction of movement of the branch when the tool is being closed. This feature may be used in all the aforementioned embodiments of the electrical circuit. However, it is particularly advantageous in the case of a dissecting electrode that is switched potential-free. In this case it is possible—in the coagulating mode without any dissecting effect—to produce a minimally shrunk tissue strip between two sealing seams that, in turn, are produced by the coagulating electrodes.

The coagulating instrument may contain a dissection actuating switch that is disposed to directly or indirectly actuate the dissecting voltage source. For the indirect actuation, said switch is connected, for example in a controlling manner, to an HF output voltage source of the generator that outputs a suitable HF output voltage for the operation of the instrument. This HF output voltage may be a dissecting voltage or a coagulating voltage. A transformer in the instrument may act as the dissecting voltage source or be fed by the coagulating voltage. Alternatively, the transformer may also be fed by the dissecting voltage and deliver coagulating voltage. If the control switch for actuation of the dissecting mode is actuated, the power switch that is in resting state is closed and thus connects the dissecting voltage source to the dissecting electrode.

Preferably, the dissection actuating switch and the coagulation actuating switch are locked relative to each other, so that they can only be actuated alternatively. For example, both switches may comprise a shared actuating element, for example in the form of a rocker switch. This ensures that either only the dissection actuating switch or the coagulation actuating switch is actuated.

Additional details of advantageous embodiments of the invention are the subject matter of the description or the claims and the drawings. They show in

DETAILED DESCRIPTION

Figure 1:
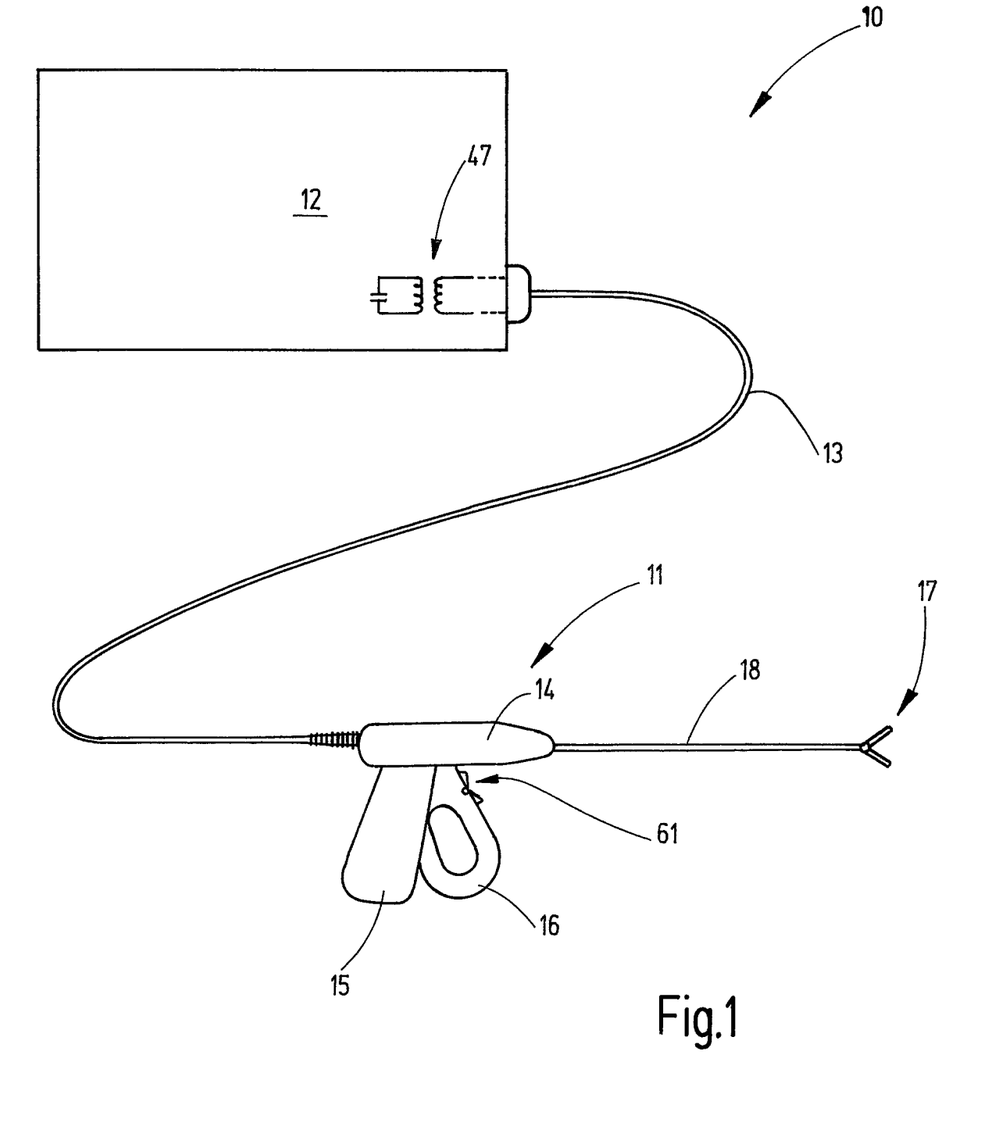
FIG. 1 a schematic representation of a coagulating and dissecting arrangement comprising a coagulating and dissecting instrument and a supply device that is connected to the instrument by means of a cable.

FIG. 1 shows a coagulation arrangement 10 that includes a coagulating and dissecting instrument 11 of laparoscopic surgery, and a device 12 for the power supply of said instrument. The instrument 11 is connected to the device 12 via a multiwire cable 13 that conducts electrical current for coagulating and/or dissecting biological tissue from the device 12 to the instrument 11 and that, furthermore, may comprise at least one signal line for conducting prompts for releasing and blocking electrical energy.

The instrument 11 comprises a housing 14 with the handle 15 and the control element 16 for actuating a tool 17 that is arranged on the distal end of a shaft 18 extending away from the housing 14. The invention may also be implemented on an instrument for open surgical applications. A shaft 18 of such an instrument can deviate from the instrument according to FIG. 1 as concerns structure and diameter and comprise an electrical circuit according to FIGS. 5 to 10. Furthermore, the invention may be implemented on an instrument 11 whose tool 17 is controlled by other means, for example by control means of a robot or the limbs of scissors or forceps that act directly on the articulated axis of the tool 17. Considering such an instrument 11, the housing 14, the handle 15 and the control element 16 may be partly omitted or be configured differently.

Figure 2:
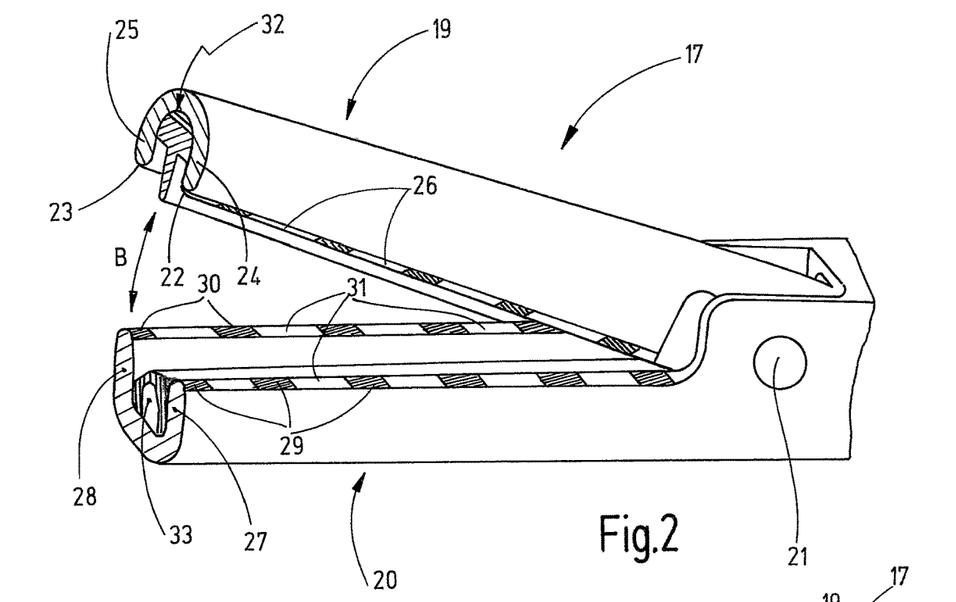
FIG. 2 a perspective representation, partially in section, of the tool of the instrument according to FIG. 1.

The tool 17 is shown in greater detail in FIG. 2. It is configured in the manner of forceps and, as such, comprises a first branch 19 and a second branch 20 that are connected to each other via a hinge 21 or another joint in such a manner that at least one of the branches 19, 20 can be moved toward or away from the other branch (20 or 19). The opening and closing movements of the branches 19, 20 are controlled by means of the control element 16, or by two manual branches in an instrument for open surgery, for example.

The first branch 19 comprises at least one coagulating electrode. In the exemplary embodiment, there are provided two first coagulating electrodes 22, 23 that are provided on the outermost ends of two limbs 24, 25 of the first branch 19 having a U-shaped cross-section. The first coagulating electrodes 22, 23 are preferably electrically connected to each other. Furthermore, they may be interrupted along the free ends of each limb 24, 25 by insulating sections 26.

The second branch 20 is configured accordingly. It also has a U-shaped cross-section with two limbs 27, 28 having second coagulating electrodes 29, 30 on their free ends. The coagulating electrodes 29, 30 or their coagulating surfaces are arranged at an angle α with respect to an imaginary plane E (FIG. 3) that extends in the direction of the longitudinal axis of the branch 20 and is supported by both limbs 27 and 28. The angle α with respect to plane E is preferably 20 degrees. The coagulating surfaces of the coagulating electrodes 29, 30 are preferably arranged so as to be inclined downward toward the support surface 39. Again, the coagulating electrodes 29, 30 can be interrupted by insulating sections 31 in order to prevent a short circuit between the branches 19, 20 when these are moved toward each other or moved into contact with each other.

Figure 3:
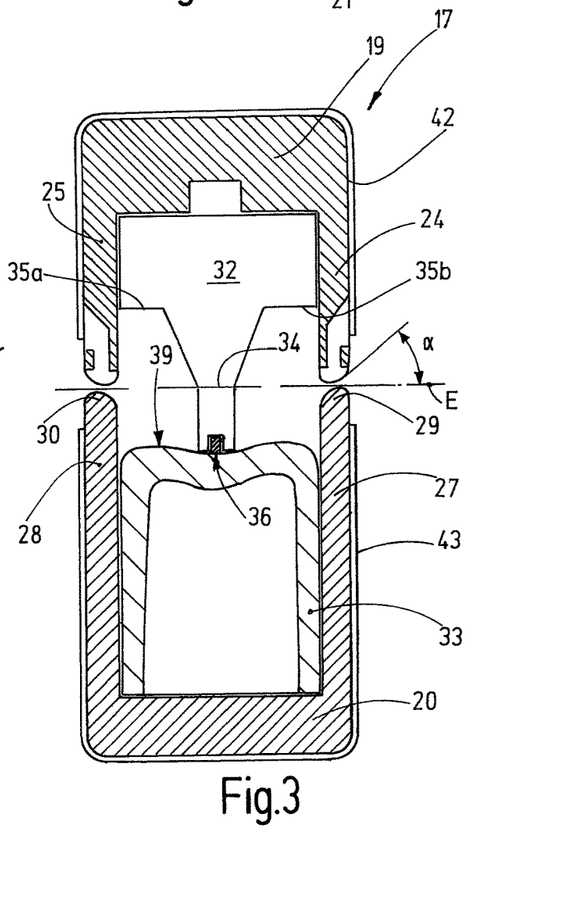
FIGS. 3 and 4 a cross-sectional view of the instrument according to FIG. 2, with and without biological tissue.

While one branch, for example the first branch 19, accommodates a dissecting electrode insert 32 in a central groove, a counterbearing element 33 is arranged on the opposite side in a corresponding groove of the second branch 20 (FIG. 3). The dissecting electrode insert 32 is made of a non-conductive material, preferably a plastic material, silicone or ceramic. It has a central wall section 34 that thickens toward its foot, said wall section extending from the limb 25 to the wall section 34 and from the wall section 34 to the limb 24. The delimiting surfaces 35a, 35b are located in a common plane and at a right angle with respect to the wall section 34, as well as at a right angle with respect to the limbs 24, 25. The limbs 24, 25 extend beyond the delimiting surfaces 35a, 35b.

On the surface that faces away from the delimiting surfaces 35a, 35b and is parallel thereto, the wall section 34 is provided with a dissecting electrode 36 that is disposed for dissecting biological tissue as needed. The dissecting electrode 36 that consists of an electrically well-conducting material is embedded in the wall section 34 consisting of insulating material and is exposed only on the side facing the counterbearing element 33. In closed state of the tool 17, the dissecting electrode 36 comes into contact with the counterbearing element 33 that comprises a tissue support surface 39 extending from one limb 28 to the other limb 27. For example, the counterbearing element 33 consists of an elastomer or another electrically insulating—preferably resiliently yielding—material, e.g., silicone.

As indicated in FIG. 3, the branches 19, 20 may be provided on their outer sides with an insulation 42, 43 in order to prevent an electrical contact with the surrounding tissue.

An electrical circuit 44 is disposed for the electrical supply of the tool 17 in conjunction with the device 12, said circuit being provided in the instrument 11, in particular in the housing 14 of said instrument. The electrical circuit 44 is shown as an example in FIG. 5. The circuit 44 comprises three output connections M, K and S that are connected to the electrodes. Specifically, the connection M acts as a connection to ground and is preferably connected to the second branch 20 and, accordingly, to the second coagulating electrodes 29, 30. In doing so, the coagulating electrodes 29, 30 form the shared electrical antipole for the dissecting electrode 36 and the first coagulating electrodes 22, 23. The output connection K is a coagulation terminal that is preferably connected to the first branch 19 and thus to the first coagulating electrodes 22, 23. The output terminal S is the connection for the dissecting voltage. This terminal is connected to the dissecting electrode 36.

Figure 5:
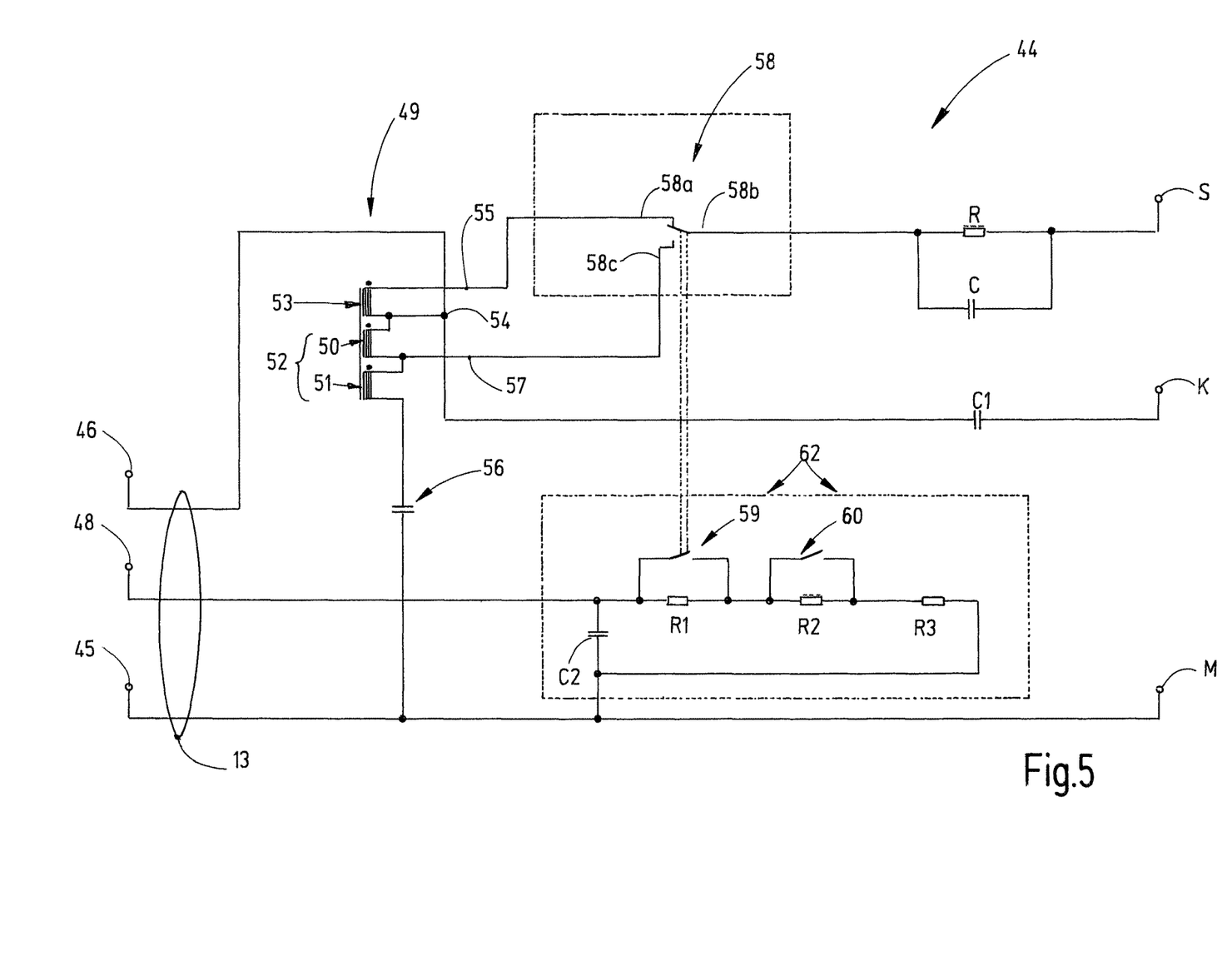
FIGS. 5 to 10 various embodiments of the electrical circuit for supplying power to the electrodes of the instrument.

On the input side, lines are lead through the cable 13 to the plug connected to the device 12, said plug having at least three connections. Two connections 45, 46 are disposed for the connection to an HF output voltage source 47 (indicated schematically in FIG. 1) that is configured as an HF generator and provides electrical energy for operating the instrument 11. A third input connection 48 is disposed for actuating or deactuating the HF output voltage source 47. The instrument contains a transformer 49 that may be configured as an autotransformer. It may comprise a primary winding 52 divided into two partial windings 50, 51, as well as a secondary winding 53 that is connected in series to the primary winding 52 based on the autotransformer principle. However, other transformer arrangements with separated primary and secondary windings are also possible.

The input connection 46 is connected to the primary winding 52, in which case this connection of the primary winding 52 represents, at the same time, a coagulating voltage source 54. In contrast, the upper end of the secondary winding 53 represents a dissecting voltage source 55. The lower end of the primary winding 52 is directly—or, if desired, via a coupling capacitor 56—connected to ground, i.e., the input connection 45 or the output connection M. The connection of the transformer 49 led out between the partial windings 50, 51 may act as the low-voltage source 57. Preferably, the number of windings of the first partial winding 50 relative to the second partial winding 51 to the secondary winding 53 is consistent with 11:11:77. In doing so, a supply voltage applied to the input connection 46 of, e.g., 100 Volts (HF) (measured to ground, i.e., input connection 45) is output as the coagulating voltage to the location forming the coagulating voltage source while the dissecting voltage source 55 delivers approximately 450 Volts measured to ground.

A conduction pathway extends from the dissecting voltage source 55 to the output connection S, i.e., to the dissecting electrode 36. On this current path there may be provided a capacitor (preferably several Nanofarad) and a resistor (several kΩ) in order to allow the detection of a spark formation. A spark formation would result in an equal proportion of the current on the connection 46 which can be detected on the device side. If a spark detection is not desirable, the resistor R, as well as the capacitor 56, may also be omitted. Furthermore, a power switch 58 with a movable contact 58b and at least one fixed contact 58a, 58c is located on the current path between the dissecting voltage source 55 and the dissecting electrode. In the present first embodiment, the power switch 58 connects—in not actuated state—the dissecting voltage source 55 to the dissecting electrode. In contrast, in actuated state, the power switch connects the dissecting electrode 36 to another voltage, for example the low-voltage source 57.

The output connection K for the coagulating voltage is connected to one of the branches, preferably the first branch 19 that also accommodates the dissecting electrode insert 32. On the current path corresponding thereto, it is possible to provide a capacitor C1. It may be disposed for limiting the coagulating current and has preferably a value of several nF. The coagulating current has preferably a frequency between 300 kHz and 400 kHz and is applied as CW (continuous wave, i.e., uninterrupted HF voltage).

The circuit 44 preferably comprises an actuating switch 62 that may be a coagulation actuating switch 59 or a dissection actuating switch 60. Both switches 59, 60 can be actuated by a shared actuating element 61, for example by a rocker (FIG. 1), so that the actuation of the actuating switch 62 closes either the dissection actuating switch 60 or the coagulation actuating switch 59, however, not both of them at the same time. In the center position of the rocker, neither of the two switches 59, 60 is closed. The switches 59, 60 may be arranged parallel to the resistors R1, R2 that are connected in series to a third resistor R3. The series circuit arrangement of the resistors R1 to R3 is preferably provided between the input connections 48, 45. In order to prevent interruptions, the resistors R1, R2, R3 may be bridged individually or, in a series connection, by one or several capacitors C2.

A bridging of one of the two resistors R1 or R2 is detected by the device connected to the connection 48 and interpreted as the prompt for actuating the HF output voltage source 47. Consequently, said voltage source is actuated during the actuation of the coagulation actuating switch 59, as well as during the actuation of the dissection actuating switch 60. If both switches 59, 60 are open, the HF output voltage source 47 is deactuated.

There exists a special feature in the mechanical connection between the coagulation actuating switch 59 and the power switch 58. They are connected in such a manner that—with the corresponding actuation of the actuating element 61—the power switch 58 initially severs the connection between the dissecting voltage source 55 and the output connection S or the dissecting electrode 36, i.e., between the contacts 58a and 58b, before the coagulation actuating switch 59 closes. In doing so, the power switch 58 preferably operates in a hysteresis-free manner. In contrast, the coagulation actuating switch 59 may exhibit a distinctly noticeable switching hysteresis in order to provide the user with tactile feedback regarding the actuation of the coagulating mode or the dissecting mode. In doing so, the hysteresis range of movement of the switch is dimensioned such that the reversal of the power switch 58 occurs outside the hysteresis range of the coagulation actuating switch 60.

Figure 4:
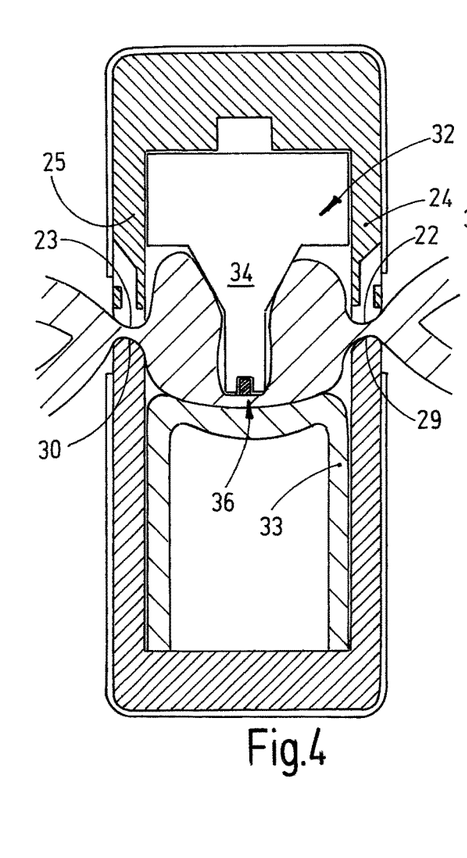

The arrangement 10 described so far operates as follows:

During operation, the instrument 11 is connected to the device 12. The user can then grasp tissue with the instrument 11 and, by actuating the control element 16, close the branches 19, 20. For example, he can grasp a hollow organ, e.g., a blood vessel which—as shown by FIG. 4—is grasped and clamped between the first coagulating electrodes 22, 23 and the second coagulating electrodes 29, 30. If now a coagulation and a dissection are to be performed simultaneously, the dissection actuating switch 60 is actuated. Now the instrument 11 receives a supply voltage that is provided as coagulating voltage on the coagulating voltage source 54 for the coagulating electrodes 22, 23. At the same time, the transformer 49 generates the dissecting voltage that is provided on the transformer output as the dissecting voltage source 55 and is conducted to the dissecting electrode 36 via the power switch 58.

If the user decides not perform a dissection and only a coagulation, he, instead, actuates the coagulation actuating switch 59. In doing so, he first reverses the power switch 58, so that the dissecting electrode 36 is connected to the low-voltage source 57. Consequently, the coagulating voltage from the coagulating voltage source 54 moves to the connection K, i.e., the coagulating electrodes 22, 23, while the dissecting electrode 36 receives a lower voltage, for example, half the coagulating voltage. In doing so, dissecting effects on the dissecting electrode 36 are minimized or prevented.

Figure 6:
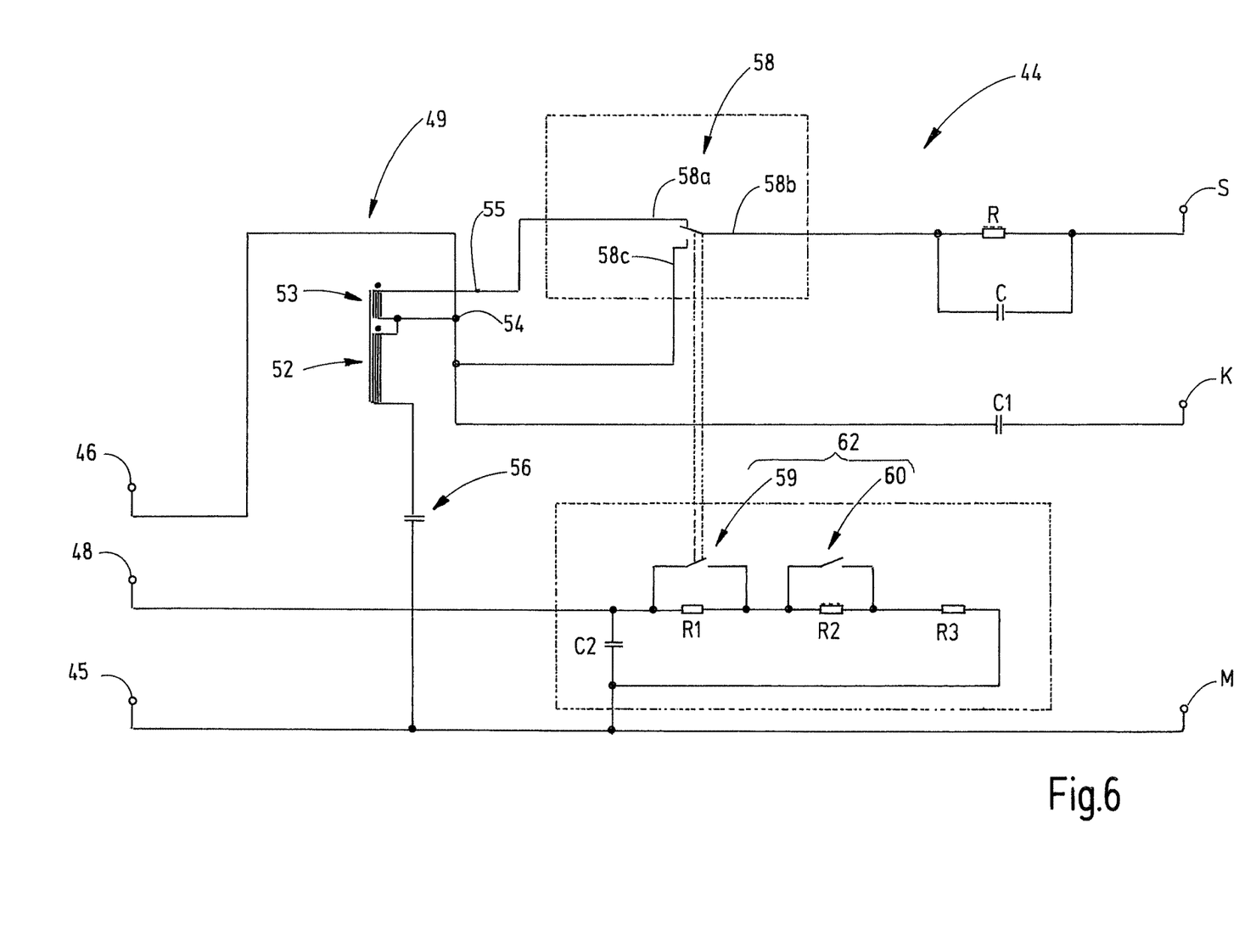

Considering the introduced circuit 44, numerous modifications are possible which, while being restricted to the differences in view of circuit 44 according to FIG. 5, will be described hereinafter:

The circuit 44 according to FIG. 6 comprises a transformer 49 with a primary winding 52 that is not divided. Consequently, the circuit 44 does not receive a low-voltage source. While the contact 58a of the power switch 58 is connected to the first end of the secondary winding 53 as above, i.e., to the dissecting voltage source 55, the contact 58c of the power switch 58 is connected to the coagulating voltage source 54. In this embodiment, an actuation of the coagulation actuating switch 59, as described hereinabove, results in a severing of the dissecting current path before the actuation of the HF output voltage source 47. A clearing of the coagulation actuating switch 59 leads to a deactivation of the HF input voltage source 47, before the dissecting current path is again closed by the switch 58. Other than that, the description provided for FIGS. 1 to 5 is applicable correspondingly and using the already introduced reference signs.

Figure 7:
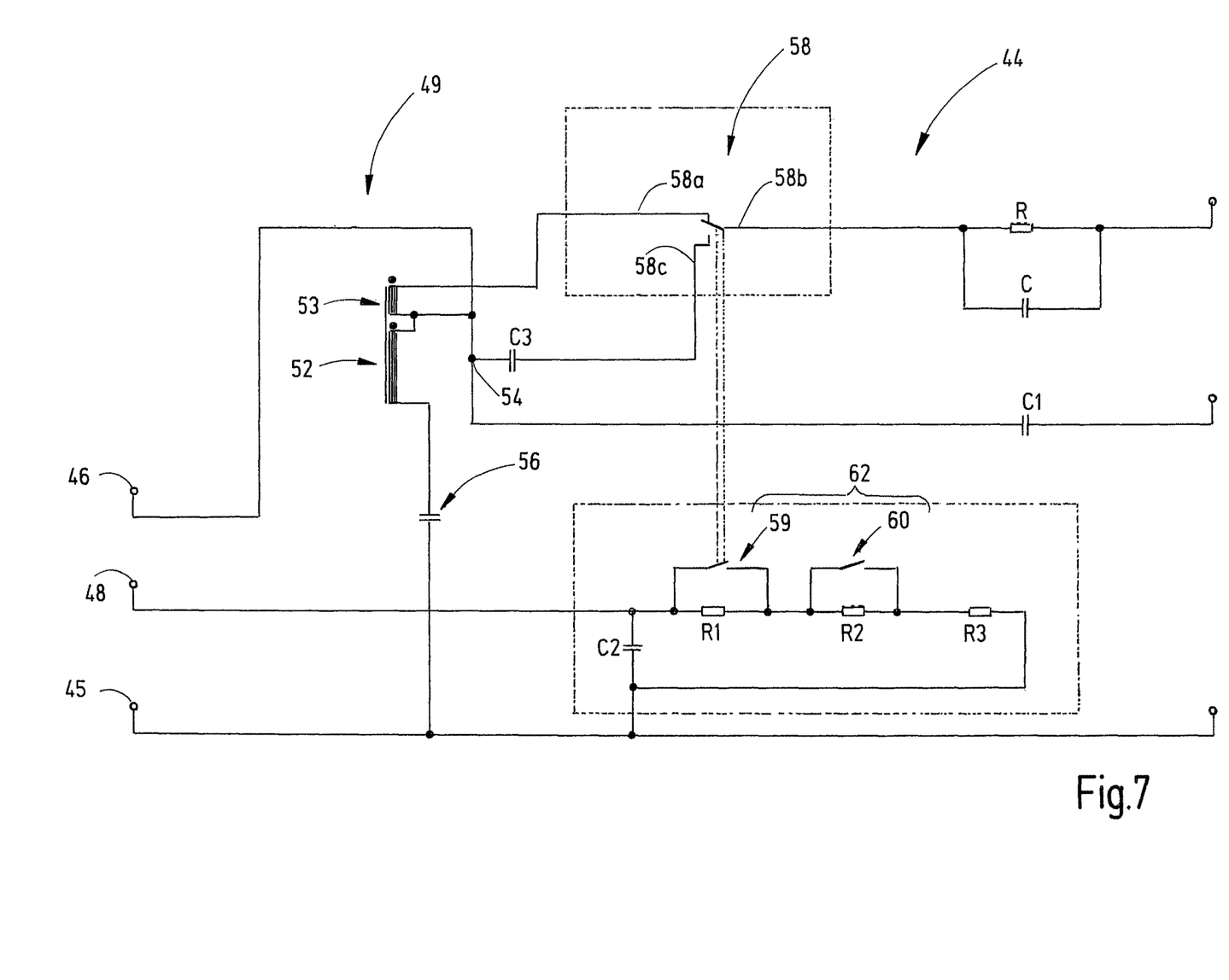

Based on the embodiment according to FIG. 6 it is possible, considering FIG. 7, to arrange a current-limiting structural element in the circuit 44 in the path leading from the coagulating voltage source 54 to the contact 58c of the power switch 58. This structural element may be a capacitor C3 or also another component, for example a coil (inductance), a resistor, or a combination of two or more such structural elements. In doing so, the impedance of the capacitor C3 or another current-limiting component is dimensioned in such a manner that the electrical current reaching the dissecting electrode 36 in the coagulating mode is limited and thus no longer has a dissecting effect. Other than that, the description provided for FIGS. 1 to 5 is applicable correspondingly and using the already introduced reference signs.

Figure 8:
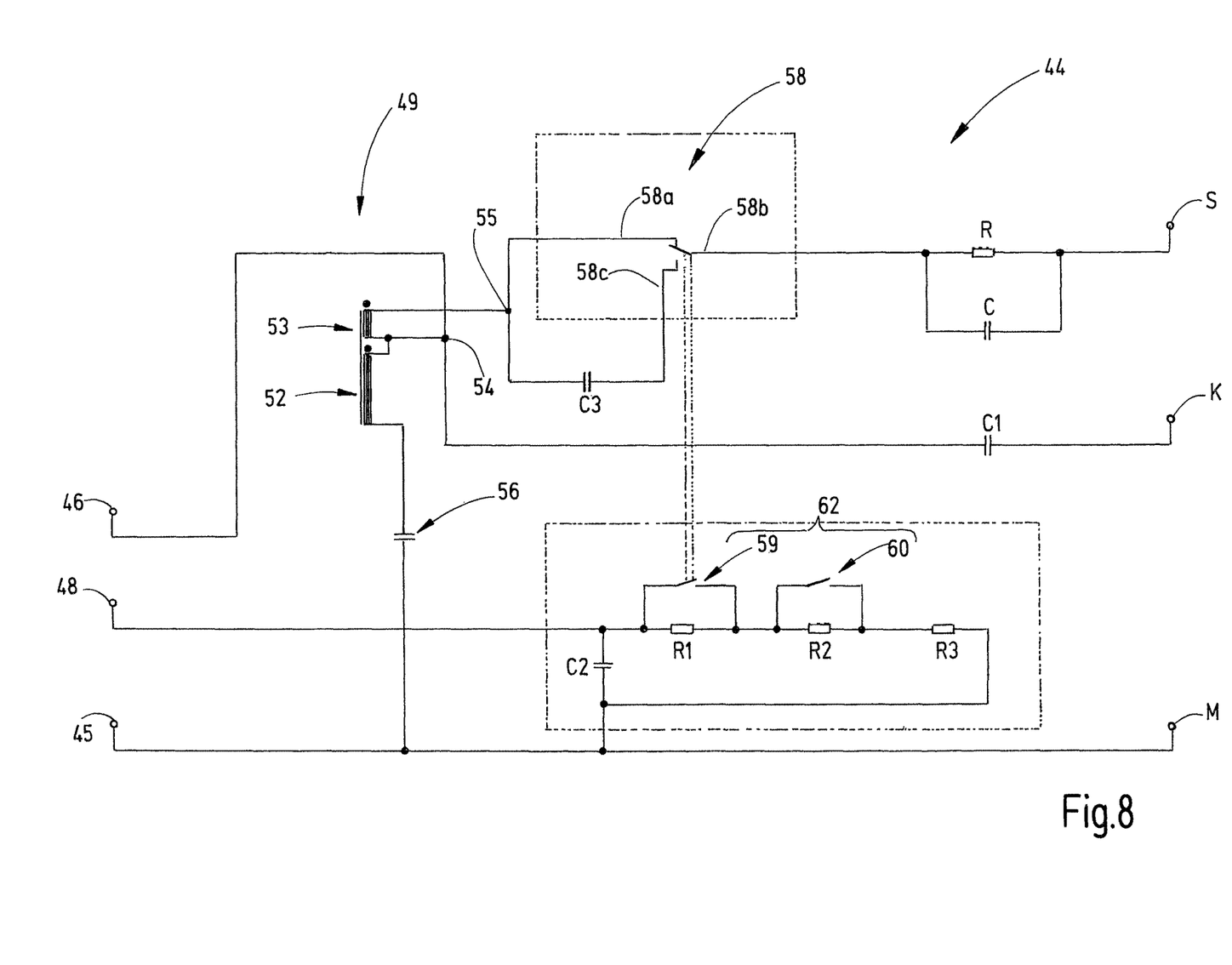

Alternatively, as shown by circuit 44 according to FIG. 8, the contact 58c of the power switch 58 may also be connected via the current-limiting component, for example the capacitor C3, to the dissecting voltage source 55. Thus, in coagulating mode, a dissecting voltage is initially applied to the dissecting electrode 36, wherein—however, —the current is limited to values that no longer allow any dissecting effect or a dissecting effect that is not worth-mentioning. Other than that, the description provided for FIGS. 1 to 5 is applicable correspondingly and using the already introduced reference signs.

Figure 9:
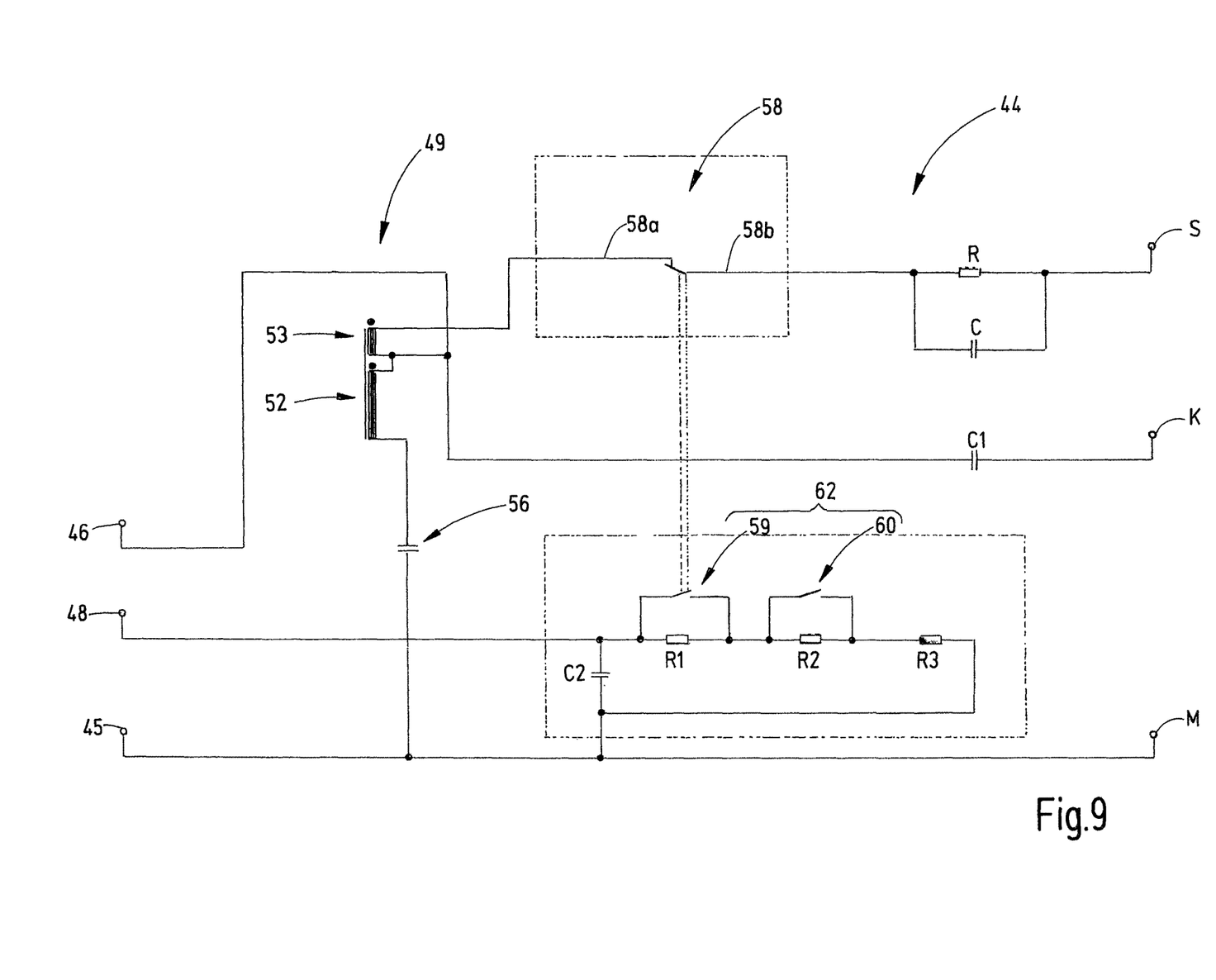

As is shown by FIG. 9, it is moreover possible to configure the power switch 58 not as a changeover switch— as is the case in all the aforementioned embodiments—but as an opener (i.e., contact 58c is missing). Again, the opener is configured upstream of the coagulation actuating switch 59, i.e., it opens before the coagulation actuating switch 59 closes, and it closes only after the coagulation actuating switch 59 has opened. In this case, the dissecting electrode in coagulating mode is potential-free and thus currentless. Other than that, the description provided for FIGS. 1 to 5 is applicable correspondingly and using the already introduced reference signs.

Figure 9A:
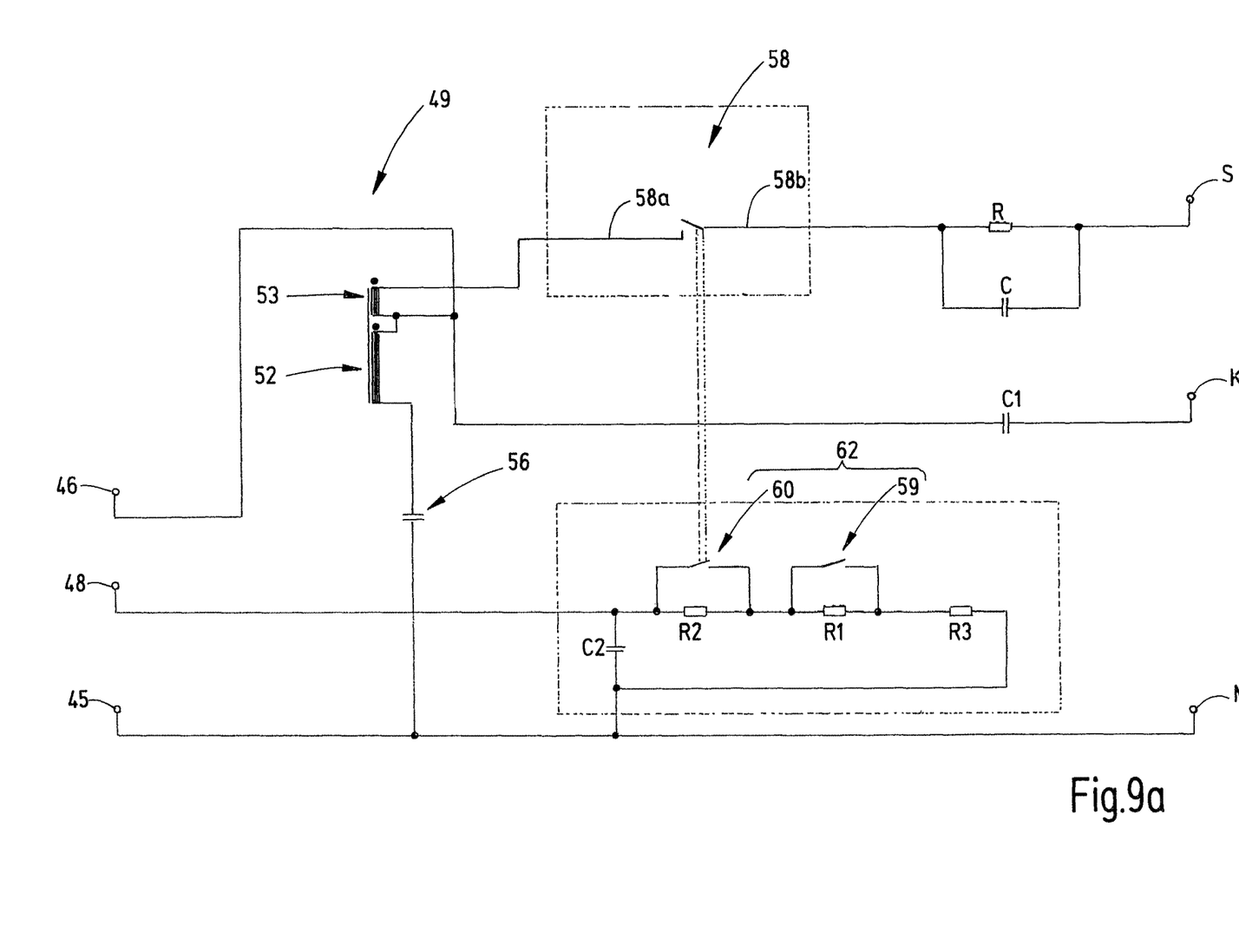
Figure 10:
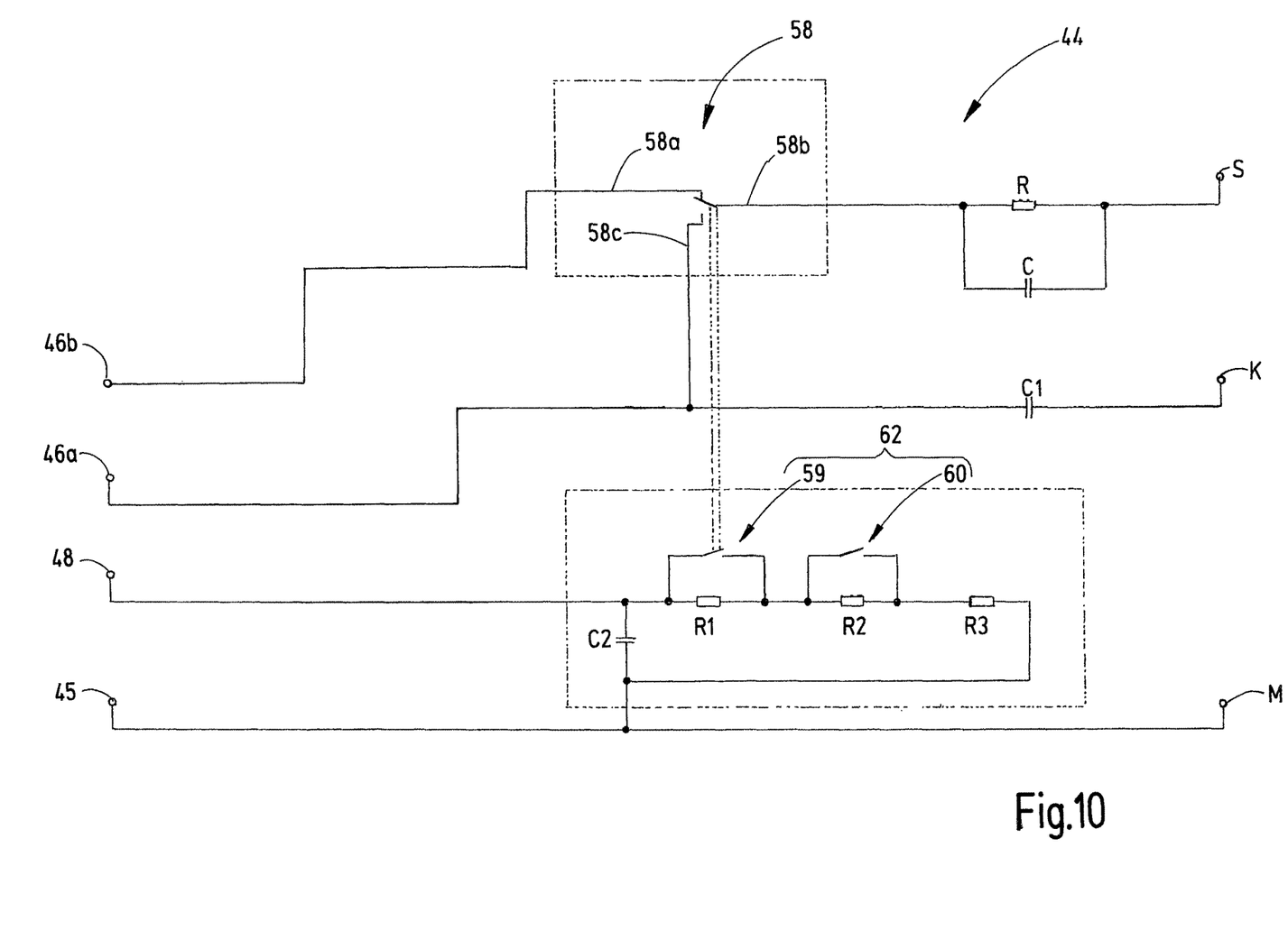

Another preferred modification of the circuit according to the invention can be seen in FIG. 9a. Referring to this embodiment, the power switch 58 is a closer that establishes a conductive connection between the contacts 58a, 58b when the dissection actuating switch 60 is actuated. The power switch precedes the dissection actuating switch 60 when closing and follows the dissection actuating switch 60 when deactuating. If, as opposed to this, only the coagulation actuating switch 59 is actuated, the power switch 58 remains open. The dissecting electrode may be currentless or may conduct a negligibly minimal current via the parasitic capacitance of the power switch 58. Other than that, the description provided for FIGS. 1 to 5 is applicable correspondingly and using the already introduced reference signs.

Considering all the embodiments of FIGS. 5, 6, 7, 8 and 10, it is also possible for the mechanical connection to exist alternatively—instead of between the power switch 58 and the coagulation actuating switch 59—between the power switch 58 and the dissection actuating switch 60. In resting state, the contact 58b is then connected to the contact 58c. If now the dissection actuating switch 60 is actuated, the power switch 58 reverses first in order to establish the connection between the contact 58a and the contact 58b before closing the dissection actuating switch 60. Upon deactuation, the power switch 58 reverses subsequently. During the actuation of the coagulation actuating switch 59 the power switch 58 remains in resting state, and thus the contact 58b continues to be connected to the contact 58c.

Whereas in all the above-described embodiments of the circuit 44 the coagulating voltage source 54 and the dissecting voltage source 55 were part of the circuit 44, it is also possible to provide the two voltage sources in the device 12. Instead of one connection 46 being disposed for the connection to an HF output voltage source, two connections 46a, 46b are provided on the plug; see FIG. 10. In this event, the connection 46a is connected to a coagulating voltage source provided in the device 12, and the connection 46b is connected to a dissecting voltage source provided in the device 12. Both are actuated at the same time by actuating one of the switches 59, 60, in which case the power switch 58—as described hereinabove—is switched in the same switching sequence to the coagulation actuating switch 59 and thus suppresses any dissecting effect in coagulating mode. Alternatively, the power switch 58 may also be connected to or coupled with the dissection actuating switch 60 and, in resting state, the contact 58b may be connected to the contact 58c in the power switch 58 (not shown). In this alternative design, the power switch 58 is reversed first when the dissection actuating switch 60 is actuated, so that the dissecting effect is allowed in dissecting mode. When the dissection actuating switch 60 is released the power switch 58 subsequently resets into resting state, so that during a subsequent coagulation actuation the dissecting effect remains suppressed. Other than that, the description provided for FIGS. 1 to 5 is applicable correspondingly and using the already introduced reference signs.

The coagulation arrangement 10 according to the invention comprises an instrument 11 having a tool 17 comprising coagulating electrodes 22, 23, 27, 28, as well as a dissecting electrode 36. The electrodes are powered by a circuit 44 that comprises a coagulating voltage source 54 and a dissecting voltage source 55, or that can be connected to such sources. The device comprises a dissection actuating switch 60 and a coagulation actuating switch 59. The latter is connected to a power switch 58 that—in coagulating mode—separates the current path from the dissecting voltage source 55 to the dissecting electrode, before the coagulating voltage source 54 is actuated. Thus, the user is presented with a reliable means in a simple manner in order to be able to more flexibly perform more complex operations.

The coagulation arrangement 10 according to the invention comprises an instrument 11 having a tool 17 comprising coagulating electrodes 22, 23, 27, 28, as well as a dissecting electrode 36. The electrodes are powered by a circuit 44 that comprises a coagulating voltage source 54 and a dissecting voltage source 55, or that can be connected to such sources. The device comprises a dissection actuating switch 60 and a coagulation actuating switch 59. The former is connected to a power switch 58 that—in dissecting mode—connects the current path from the dissecting voltage source 55 to the dissecting electrode 36, before the dissecting voltage source 55 or the HF output voltage source 47 and the coagulating voltage source 54 are actuated. Thus, the user is presented with a reliable means in a simple manner in order to be able to more flexibly perform more complex operations.

LIST OF REFERENCE SIGNS

| | |
|---|---|
| 10 | Coagulation arrangement |
| 11 | Instrument for coagulating and dissecting biological tissue |
| 12 | Device |
| 13 | Cable |
| 14 | Housing |
| 15 | Handle |
| 16 | Control element |
| 17 | Tool |
| 18 | Shaft |
| 19 | First branch of the tool 17 |
| 20 | Second branch of the tool 17 |
| 21 | Hinge |
| 22, 23 | First coagulating electrodes |
| 24, 25 | Limb of the first branch 19 |
| 26 | Insulating sections |
| 27, 28 | Limbs of the second branch 20 |
| 29, 30 | Second coagulating electrodes |
| 31 | Insulating sections |
| 32 | Dissecting electrode insert |
| 33 | Counterbearing element |
| 34 | Central wall section |
| 35a, 35b | Delimiting surface |
| 36 | Dissecting electrode |
| 39 | Support surface |
| 42, 43 | Insulation |
| 44 | Circuit |
| M, K, S | Output connections |
| 45, 46 | Input connections of the circuit 44 |
| 47 | HF output voltage source (HF generator) |
| 48 | Input connection |
| 49 | Transformer |
| 50, 51 | Partial windings |
| 52 | Primary winding |
| 53 | Secondary winding |
| 54 | Coagulating voltage source |
| 55 | Dissecting voltage source |
| 56 | Coupling capacitor |
| 57 | Low-voltage source |
| C, C1, C2, C3 | Capacitors |

| | |
|---|---|
| R, R1, R2, R3 | Resistors |
| 58 | Power switch |
| 58a | Fixed contact of the switch 58 (normally closed contact) |
| 58b | Movable contact of the switch 58 |
| 58c | Fixed contact of the switch 58 (normally open contact) |
| 59 | Coagulation actuating switch |
| 60 | Dissection actuating switch |
| 61 | Actuating element |
| 62 | Actuating switch |

The invention claimed is:

1. An instrument for coagulating and, if needed, for dissecting biological tissue, with a tool comprising:
   at least one first and at least one second coagulating electrode which can be moved relative with respect to each other for grasping the biological tissue therebetween, and comprising at least one dissecting electrode for dissecting the biological tissue grasped between the at least one first and the at least one second coagulating electrode;
   an electrical circuit that is connected to the at least one first and the at least one second coagulating electrode and to the at least one dissecting electrode and configured to be connected to a dissecting voltage source and a coagulating voltage source;
   wherein the electrical circuit comprises
      an input side including first and second input connections, wherein the first and second input connections are configured for connection with a high frequency (HF) output voltage source for providing electrical energy for operating the instrument;
      a transformer electrically connected to the first and second input connections, the transformer configured to simultaneously provide the dissecting voltage source and the coagulating voltage source;
      first, second, and third output connections, wherein the first output connection is connected to the at least one second coagulating electrode and to ground;
      wherein the second output connection is a coagulating connection that is connected to the at least one first coagulating electrode; and
      wherein the third output connection is a dissecting connection that is connected to the dissecting voltage source and to the at least one dissecting electrode;
      a power switch disposed in a current path between the dissecting voltage source and the at least one dissecting electrode configured to selectively disconnect the at least one dissecting electrode from the dissecting voltage source or to selectively connect the at least one dissecting electrode to the dissecting voltage source; and
      an actuating switch for selectively actuating the high frequency (HF) output voltage source;
   wherein the actuating switch and the power switch are controlled in series by a shared actuating element wherein actuation of the shared actuating element initiates one of a dissecting mode, wherein the power switch is closed to connect the at least one dissecting electrode to the dissecting voltage source and the actuating switch is subsequently closed to actuate the high frequency output voltage source, and a coagulation mode, wherein the power switch is opened to disconnect the at least one dissecting electrode from the dissecting voltage source and the actuating switch is subsequently closed to actuate the high frequency output voltage source;
   wherein in the dissecting mode, the at least one dissecting electrode is energized by the dissecting voltage source and the at least one first coagulating electrode is energized by the coagulating voltage source simultaneously.

2. The instrument according to claim 1, wherein the power switch and the actuating switch are connected to the actuating element in such a manner that, upon actuating the actuating element, the power switch closes before the actuating switch closes, and that, upon clearing the actuating element, the actuating switch opens before the power switch opens.

3. The instrument according to claim 1 wherein, in a resting state, the power switch does not provide an electrical connection between the dissecting voltage source and the at least one dissecting electrode and, in an actuated state, connects the at least one dissecting electrode to the dissecting voltage source.

4. The instrument according to claim 3, wherein, in the resting state, the power switch connects the at least one dissecting electrode to the coagulating voltage source or to a low-voltage source, or is switched potential-free.

5. The instrument according to claim 4, wherein, in the resting state, the power switch connects at least one dissecting electrode to a low-voltage source, wherein the low-voltage source is the transformer that is connected on a primary side thereof to the coagulating voltage source.

6. The instrument according to claim 3, wherein, in resting state, the power switch connects the at least one dissecting electrode to a current-limiting means.

7. The instrument according to claim 1, wherein the instrument comprises a coagulation actuating switch that is disposed for actuating the HF output voltage source.

8. The instrument according to claim 1, wherein the instrument comprises a dissection actuating switch that is disposed for actuating the HF output voltage source.

9. The instrument according to claim 7, further comprising a dissection actuating switch that is disposed for actuating the HF output voltage source;
   wherein the dissection actuating switch and the coagulation actuating switch are configured such that they can only be alternatively actuated.

10. The instrument according to claim 1, wherein the transformer is connected or is configured to be connected to the coagulating voltage source.

11. The instrument according to claim 1, wherein the coagulating voltage source is arranged outside the instrument.

12. The instrument according to claim 1, wherein the input side of the electrical circuit further comprises a third input connection, wherein the third input connection is configured for activating or deactivating the high frequency (HF) output voltage source.

* * * * *